US006572549B1

(12) United States Patent
Jong et al.

(10) Patent No.: US 6,572,549 B1
(45) Date of Patent: Jun. 3, 2003

(54) HIGH FRAME RATE EXTENDED FIELD OF VIEW ULTRASOUND IMAGING SYSTEM AND METHOD

(75) Inventors: Jing-Ming Jong, Seattle, WA (US); Paul Detmer, Seattle, WA (US)

(73) Assignee: Koninklijke Philips Electronics NV (NL)

( * ) Notice: Subject to any disclaimer, the term of this patent is extended or adjusted under 35 U.S.C. 154(b) by 6 days.

(21) Appl. No.: 10/025,288

(22) Filed: Dec. 18, 2001

(51) Int. Cl.[7] .................................................. A61B 8/00
(52) U.S. Cl. ....................................... 600/443; 128/916
(58) Field of Search ................................. 600/437, 440, 600/441, 442, 443, 447, 450–471; 128/916; 367/7, 11, 130, 138; 73/625, 626

(56) References Cited

U.S. PATENT DOCUMENTS

| | | | |
|---|---|---|---|
| 5,566,674 A | 10/1996 | Weng ..................... | 128/660.07 |
| 5,575,286 A | 11/1996 | Weng et al. ............. | 128/653.1 |
| 5,582,173 A | 12/1996 | Li .......................... | 128/660.07 |
| 5,655,535 A | 8/1997 | Friemel et al. ......... | 128/660.07 |
| 5,782,766 A | 7/1998 | Weng et al. ............. | 600/443 |
| 5,876,342 A | 3/1999 | Chen et al. .............. | 600/443 |
| 5,885,218 A | 3/1999 | Teo et al. ................. | 600/443 |
| 5,899,861 A | 5/1999 | Friemel et al. ......... | 600/443 |
| 6,014,473 A | 1/2000 | Hossack et al. ........ | 382/294 |
| 6,110,114 A | 8/2000 | Nock et al. ............. | 600/443 |
| 6,117,081 A | 9/2000 | Jago et al. ............... | 600/443 |
| 6,126,598 A | 10/2000 | Entrekin et al. ........ | 600/437 |
| 6,132,376 A | 10/2000 | Hossack et al. ........ | 600/443 |
| 6,159,152 A | 12/2000 | Sumanaweera et al. . | 600/443 |
| 6,193,662 B1 | 2/2001 | Hwang ................... | 600/447 |
| 6,238,345 B1 | 5/2001 | Wissler et al. .......... | 600/443 |
| 6,283,917 B1 | 9/2001 | Jago et al. ............... | 600/437 |
| 6,299,579 B1 | 10/2001 | Peterson et al. ........ | 600/443 |

OTHER PUBLICATIONS

Tuthill, Theresa A., et al., "Automated Three–dimensional US Frame Positioning Computed from Elevational Speckle Decorrelation", Radiology, vol. 209, No. 2, Nov. 1998, pp. 575–582.

Primary Examiner—Marvin M. Lateef
Assistant Examiner—Ali M. Imam
(74) Attorney, Agent, or Firm—Dorsey & Whitney LLP

(57) ABSTRACT

A 3-D ultrasound imaging system acquires partially complete image volumes interspersed with substantially complete image volumes. The partially complete image volumes contain speckle that is processed by a cross-correlation algorithm to track the movement of an ultrasound scanhead. By tracking the movement of the scanhead, the substantially complete image volumes can be properly registered with each other and combined to create a 3-D extended field of view image. The partially complete image volumes contain significantly less data than the substantially complete image volumes. Therefore, the partially complete image volumes can be acquired more quickly than the substantially complete image volumes to allow the scanhead to be scanned at a relatively fast speed.

34 Claims, 6 Drawing Sheets

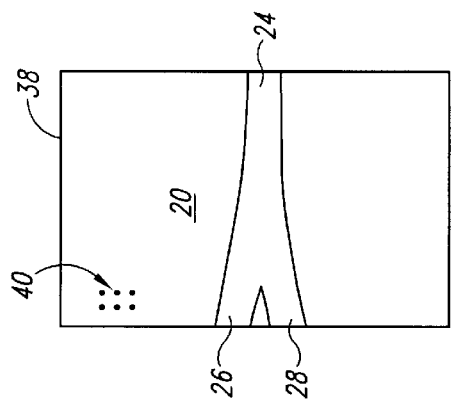
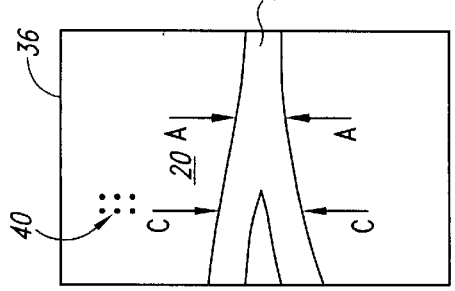
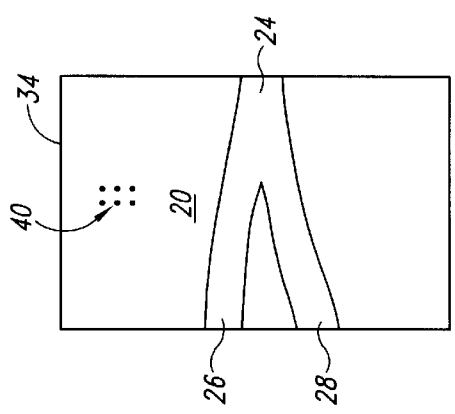
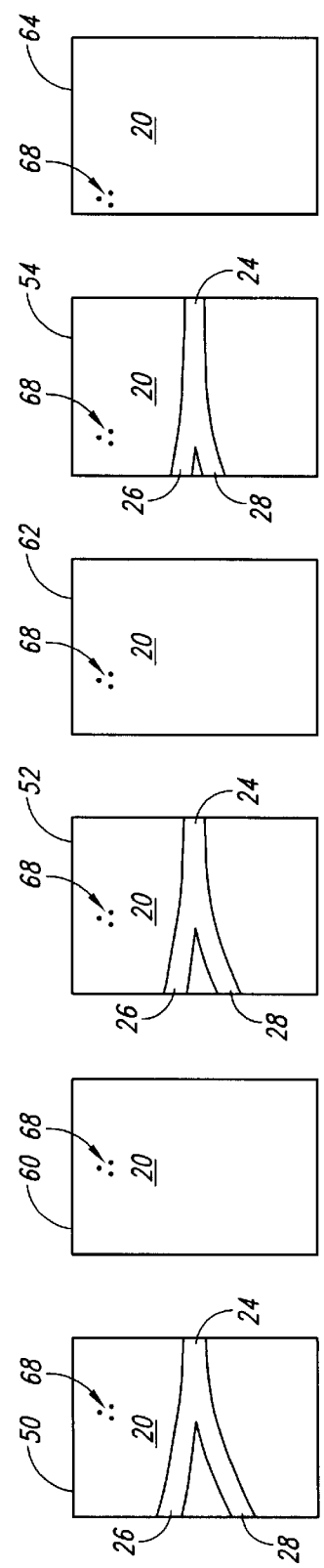

HIGH FRAME RATE EXTENDED FIELD OF VIEW ULTRASOUND IMAGING SYSTEM AND METHOD

TECHNICAL FIELD

This invention relates to ultrasound diagnostic imaging systems and, in particular, to a method and apparatus for rapidly obtaining extended field of view ultrasound images.

BACKGROUND OF THE INVENTION

Diagnostic ultrasound systems are commonly used to generate two-dimensional ("2-D") and three-dimensional ("3-D") images of tissues, vessels and organs within a patient's body. To do so, a sonographer positions an ultrasound scanhead having an array of transducer elements adjacent to a target area. The transducer elements emit ultrasound energy that propagates into the patient where it is absorbed, dispersed, refracted, and reflected by internal structures. Reflected ultrasound energy is received back at the scanhead where it is converted back into electronic signals. An image is then created from the electronic signals.

The received electronic signals undergo beamforming to coordinate the samples in time and space to a target area. Exemplary beamforming methods for controlling the imaging process include focus, steering, apodization and aperture. Focus is a time delay profile of active transducer elements. Steering is the control of focus depth points along azimuth and elevation axes of the transducer elements. Apodization is a voltage weighting profile of active transducer elements. Aperture is the control of the number of transducer elements that are active along an axis of the scanhead. The beamformed signals are processed to display an image showing echo and Doppler flow information, which may be in the form of a cross-sectional image.

A conventional cross-sectional image is a brightness image (i.e., referred to as a "B-mode" or "B-scan" image) in which component pixels are brightened in proportion to the intensity of a corresponding echo signal. Existing B-scan ultrasound imaging systems use scanheads having one-dimensional linear arrays to generate B-scan images of the body. The images produced by B-scan ultrasound imaging systems are composed of discrete image frames, the characteristics of which depend on the number of transducer elements that are active, the relative spacing of the elements and the steering and focus of the transducer elements. Each B-scan image frame represents a two-dimensional ("2D") image plane that is taken through a cross-section of the body that extends inwardly from the linear transducer array.

A drawback of such B-scan imaging is that most of the imaged tissues or vessels appear only as cross sections since most tissues or vessels of interest do not extend along the image plane. It is therefore often difficult using B-scan imaging to visualize tissues or vessels extending through the body at approximately a constant distance from a skin surface with which the scanhead is in contact.

One approach to making B-scan imaging more useful is to combine a large number of 2-D image frames to create an "extended field of view" ("EFOV") or "panoramic" image. In these systems, the scanhead is moved along a skinline to produce successive 2-D B-scan image frames that represent respective spatially offset 2-D image planes, as explained above. Each image plane is defined by a centerline of the scanhead array, i.e., the path along which the ultrasound is directed, and a direction that extends along the axis of the transducer array. The scanhead is scanned in a direction extending along the axis of the array to create a series of 2-D B-scan image frames. The image frames lie in a common plane and have regions that spatially overlap each other. The image frames are then combined by registering the overlapping areas of adjacent image frames. The resulting image is a 2-D EFOV B-scan image lying in a plane extending in the scanning direction. Alternatively, the scanhead may be scanned in a direction that is perpendicular to the axis of the array to create a series of B-scan image frames that lie in different planes that are parallel to each other. The image frames are obtained sufficiently close to each other that beam patterns of the frames spatially overlap each other in elevation. The image frames are then combined by registering the adjacent image frames. The resulting image is a 3-D EFOV B-scan image containing all of the B-scan image frames.

In order to make proper registration of the image frames possible, accurate information about the distance between adjacent frames must be known. Early EFOV imaging systems, known as "B-arm scanning systems," included a single beam ultrasound scanhead mounted at the end of an articulated arm. The joints of the articulated arm contained sensors that produced an electrical signal indicative of the spatial position of the scanhead. As the scanhead was scanned over the body of the patient, an image frame was produced from the ultrasound returns obtained from the scanhead and the relative spatial locations of the scanhead while the returns were being obtained. The image frames from multiple adjacent scans of the scanhead were computed and stored, and then assembled in consecutive, side-by-side locations to create an EFOV image. These early EFOV systems were capable of generating an ultrasound image that could laterally extend for the maximum number of successive image frames that the system could store and display and extend vertically over the range of positions that arm could extend.

EFOV imaging systems relying on hardware position sensors have several shortcomings. First, position sensors based on electromagnetic energy emissions may interfere with the transmitted and received ultrasound energy. Other hardware position sensors tend to be less accurate requiring longer and more frequent calibration processes. Also, it is a challenge to integrate the sensor's detection scheme into the ultrasound image capturing process. The position sensor captures data samples. Such samples need to be synchronized to the ultrasound sampling process and the ultrasound data processing data. Finally, EFOV imaging systems having scanheads mounted at the end of an arm are cumbersome to operate because the arm tends to restrict freedom of movement.

In recent years, systems have been developed for electronically registering B-scan images to produce an EFOV image. As previously explained, the scanhead in these systems is scanned along a skinline to produce successive, spatially offset 2-D image frames, . Each image frame is spatially registered with a previously acquired overlapping image frame, and the image frames are then combined to produce an EFOV image that is laterally extensive in the direction of motion of the scanhead.

One conventional technique for producing a 2-D EFOV B-scan image is shown in FIG. 1. An ultrasound scanhead 10 having a linear array of transducer elements 12 is placed in contact with a skinline 14 of a patient. The ultrasound scanhead 10 is coupled to an imaging system (not shown in FIG. 1) by a cable 16. In the example shown in FIG. 1, the ultrasound scanhead 10 is being used to scan tissues 20 beneath the skinline 14 containing a blood vessel 24 that divides into two branches 26, 28 at one end. However, it will be understood that the ultrasound scanhead 10 can likewise be used to scan other blood vessels as well as tissues, vessels or organs.

To scan a length of the blood vessels 24, 26, 28, the sonographer slides the ultrasound scanhead 10 in the direction 30. With reference, also, to FIG. 2, as the ultrasound scanhead 10 is moved in the direction 30, successive 2-D B-scan image frames 34, 36, 38 lying in substantially the same plane are acquired. Each of the image frames 34, 36, 38 is composed of data from ultrasound echoes returned from all locations in a thin volume represented by the image frame. Each image frame 34, 36, 38 is slightly displaced from the previous image frame in the direction 30. The magnitude of the image frame displacement is a function of the speed the scanhead 10 is moved and the rate at which image frames 34, 36, 38 are acquired. As explained in greater detail below, the displacement between successive image frames 34, 36, 38 is computed and the image frames are registered and combined on the basis of the displacements to produce a 2-D EFOV B-scan image of the tissues 20 and blood vessels 24, 26, 28. It is therefore important for adjacent image frames 34, 36, 38 to overlap each other at least slightly so that they can be properly registered with each other by suitable means, such as cross-correlation techniques.

The image frames 34, 36, 38 are individually shown in respective FIGS. 3A–C. As shown in FIG. 3B, the image frame 36 overlaps the image frame 34 starting at point A, and it overlaps the image frame 38 starting point C. In practice, the image frames 34, 36, 38 would generally overlap each other to a greater degree than shown in FIG. 2, but doing so in FIG. 2 would make it difficult to visualize the individual image frames 34, 36,38.

Ideally, it is desirable for the ultrasound scanhead 10 to be translated at a constant speed while image frames 34, 36, 38 are being acquired so that individual image frames 34, 36, 38 are not stretched or compressed laterally relative to earlier acquired image frames 34, 36, 38. It is also desirable for the scanhead 10 to be moved in a single plane so there is high correlation from each image frame 34, 36, 38 to the next. However, manual scanning over an irregular body surface often causes departures from either or both of these desirable conditions. Either or both of these effects of less than desirable manual scanning can be compensated for by conventional means. It will also be understood that image frames 34, 36, 38 can be obtained using an ultrasound scanhead that is structurally different from the ultrasound scanhead 10 shown in FIG. 1.

The adjacent image frames are typically registered with each other by using a cross-correlation algorithm to identify corresponding structures in each image frame. The corresponding structures may be patterns in tissues or vessels, or may be speckle present in the 2-D images. Speckle results when an ultrasound beam transmitted into the body is scattered by microstructures that are too small to be resolved by the ultrasound beam, i.e., approximately smaller than the wavelength of the ultrasound. Although the microstructures are too small to be resolved by the ultrasound beam, the microstructures nevertheless disperse, reflect, or otherwise interfere with the signal that is returned to the scanhead. When an image is created based on the returned ultrasound signal, this interference, which is noise known as "speckle" causes the image to appear granular. As shown in FIGS. 3A–C, each of the image frames 34, 36, 38 contain speckle 40, in addition to the vessels, tissues or blood flow being imaged. The speckle 40 appearing in each image frame 34, 36, 38 is substantially identical for corresponding locations in the underlying tissues 20 since the speckle 40 is caused by stationary microstructures, as previously explained. Therefore, the speckle 40 is present in each of the image frames 34, 36, 38 at locations that are spatially offset by the movement of the scanhead 10 from one image frame 34, 36, 38 to the next. The speckle 40 can then be used to properly register the image frames 34, 36, 38 with each other, as shown in FIG. 4. Adjacent image frames 34, 36, 38 can be properly registered with each other by suitable techniques, such as using a cross-correlation algorithm to identify corresponding structures in each image frame. The adjacent image frames are then registered with each other by electronically placing the corresponding structures in the same position. Although the speckle 40 is shown in FIGS. 3A–3C as being in only one location in each of the image frames 34, 36, 38, it will be understood that much of the image frame will normally contain some speckle.

One problem with EFOV imaging systems using electronic registration results from the time required to process the image frames 34, 36, 38 to determine proper registration. Cross-correlation algorithms typically used to properly register the image frames 34, 36, 38 are computationally intensive and thus require a substantial period of time even when using high-speed processors. The time required for the cross-correlation algorithm to properly register adjacent image frames 34, 36, 38 limits the frame rate, i.e., the speed at which image frames can be acquired. Limiting the frame rate, in turn, limits the speed at which the scanhead 10 may be scanned in order to acquire an image. As a result, it can take a substantial period of time to acquire an image using EFOV imaging systems. Furthermore, it can be difficult for even a trained operator to move the scanhead 10 at the proper speed. Moving the scanhead 10 too quickly can result in insufficient overlap between adjacent image frames 34, 36, 38 to properly register the image frames. Moving the scanhead 10 too slowly only serves to further increase the considerable time needed to acquire an EFOV image.

The time required to acquire an EFOV image could be reduced by reducing the number of 2-D image frames 34, 36, 38 that are combined to create the EFOV image. However, reducing the number of 2-D image frames 34, 36, 38 used to form the EFOV image can seriously degrade the quality of the resulting EFOV image.

Although the problem with conventional EFOV imaging systems has been explained with respect to 2-D EFOV B-scan images formed by combining 2-D Bscan image frames, it also exists when forming a three dimensional (3-D) EFOV image. For example, the rate at which a 3-D EFOV image can be formed by combining 3-D image volumes is also limited by the time needed to properly register the 3-D image volumes. As another example, it also requires a great deal of time to properly register 2-D Doppler image frames or 3-D Doppler image volumes used to form a 3-D EFOV Doppler image.

There is therefore a need for a system and method for allowing image frames to be rapidly acquired and registered, thereby allowing high-quality EFOV images to be quickly obtained, particularly when producing 3-D EFOV images.

SUMMARY OF THE INVENTION

A method and system for displaying an extended field of view image includes an ultrasound scanhead that is scanned across a target area. While the target area is being scanned, data are acquired corresponding to substantially the entire portion of each image frame or volume in a first set of spatially overlapping ultrasound image frames or volumes.

During the scan, data are also acquired corresponding to a relatively small part of each image frame or volume in a second set of spatially overlapping ultrasound image frames or volumes that are interspersed with the image frames or volumes in the first set. Speckle that is present in at least the image frames or volumes in the second set is then used to determine the displacement of the scanhead from respective positions where the data for each of the image frames or volumes are acquired. Based upon these displacement determinations, data corresponding to the image frames or volumes in the second set are processed to create image data corresponding to the image frames or volumes in the first set combined and registered with each other. This image data corresponds to an extended field of view image that can be then displayed.

BRIEF DESCRIPTION OF THE DRAWINGS

FIGS. 3A–C are plan views individually showing each of the 2-D image frames obtained as shown in FIG. 2.

FIG. 4 is a plan view showing a technique for producing a 2-D EFOV B-scan image from several 2-D B-scan image frames according to one embodiment of the invention.

DETAILED DESCRIPTION OF THE INVENTION

Figure 1:
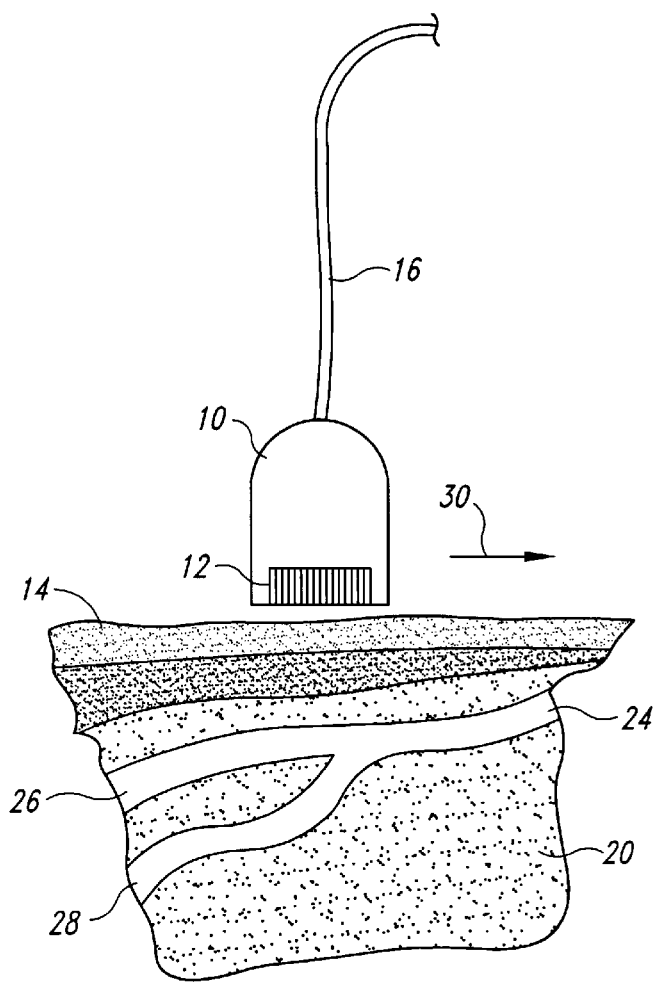
FIG. 1 is a schematic view showing tissues containing a blood vessel being scanned by a conventional ultrasound scanhead to acquire 2-D B-scan image frames used to create a 2-D B-scan extended field of view image.
Figure 2:
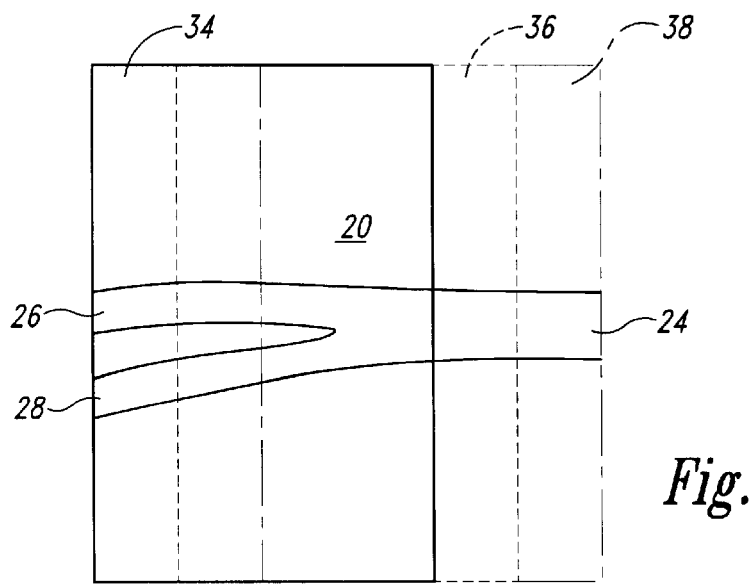
FIG. 2 is a plan view showing a plurality of 2-D image frames being obtained by scanning as shown in FIG. 1.
Figure 5:
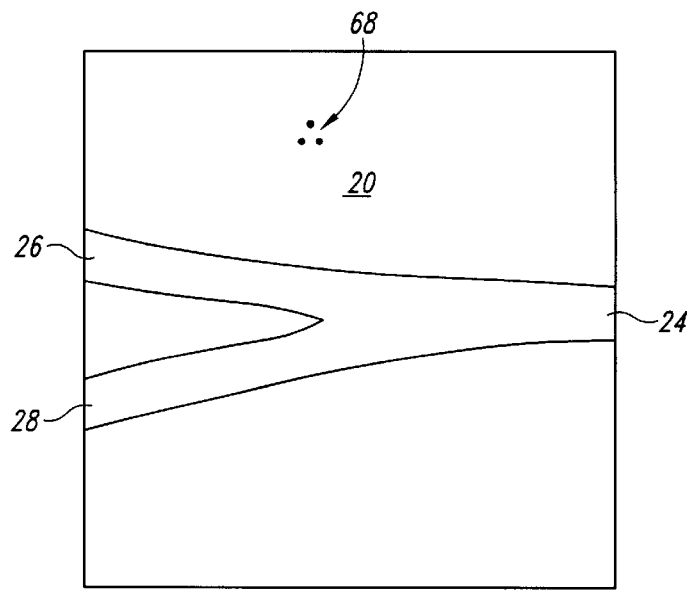
FIG. 5 is a plan view showing the 2-D B-scan image frames of FIGS. 5 properly registered with each other according to one embodiment of the invention.

One technique for producing a 2-D EFOV image according to one embodiment of the invention is shown in FIG. 4. Individual image frames 50, 52, 54 are acquired using the same technique shown in FIGS. 1–3. However, the scanhead 10 also acquires partial image frames 60, 62, 64 alternating with the acquisition of the image frames 50, 52, 54. The partial image frames 60, 62, 64 contain only as much of the speckle patterns in the image frames 60, 62, 64 that is needed to track movement of the scanhead. As shown in FIG. 4, each of the image frames 50–54 and 60–64 contain a speckle pattern 68 at locations in the image frames that are spatially offset by the movement of the scanhead 10 from one image frame 50–54 and 60–64 to the next. The speckle pattern 68 in all of the image frames 50–54 and 60–64 or only in the partial image frames 60–64 is then used to properly register the full image frames 50, 52, 54 with each other, as shown in FIG. 5. As with the conventional technique explained with reference to FIGS. 1–3, a conventional cross-correlation algorithm can be used to identify the location of the speckle pattern 68 in each image frame 50–54 and 60–64. The ratio in the shift in the location of the speckle pattern 68 from one image frame to the rate at which image frames are acquired corresponds to the velocity of scanhead 10 movement.

By acquiring data for only a part of the image frames 60, 62, 64, the amount of data for the image frames 60, 62, 64 is considerably less than the amount of data for the full image fames 50, 52, 54. As a result, the image frames 60–64 can be acquired significantly faster than the image frames 50–54 can be acquired. Also, since there is less data in the image frames 60–64 to be processed by the cross correlation algorithm, properly registering the image frames 50–54 requires less time. The scanhead 10 can therefore be moved more rapidly without sacrificing image quality.

Although FIG. 5 shows the partial image frames 60, 62, 64 alternating with the full image frames 50, 52, 54 on a one-to-one basis, it will be understood that the alternation ratio need not be 1:1. In fact, it may be preferable to increase to number of partial image frames 60, 62, 64 to a ratio of 2:1, 3:1 or even higher to increase the acquisition speed, as long as there are no gaps between frames 50, 52, 54.

Figures 6A, 6B:
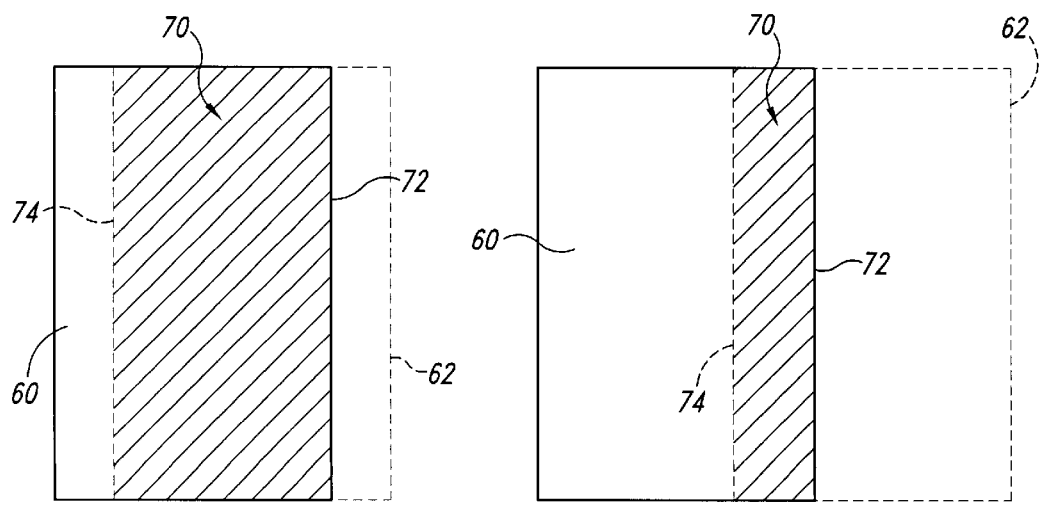
FIGS. 6A and 6B are plan views showing the manner in which image frames obtained by a scanhead overlap each other at two different scanning speeds.

Consideration should also be given to the specific areas of the partial image frames 60, 62, 64 in which image data is acquired. With reference to FIG. 6A, when the scanhead 10 is moved relatively slowly, an area of overlap 70 between the image frames 60, 62 will be fairly large. With reference to FIG. 6B, when the scanhead 10 is moved more rapidly, the area of overlap 70 between the image frames 60, 62 will be substantially smaller. However, in all cases in which there is some overlap, the overlap will be adjacent a leading edge 72 of the earlier image frame 60 and a trailing edge 74 of the later image frame 62. Thus, the areas of the partial image frames 60–64 preferably should border the leading edge 72 of the earlier image frame 60 and the trailing edge 74 of the later image frame 62. The width of the overlap 70 can be adjusted as a function of the velocity of scanhead movement and the frame rate.

Figure 7:
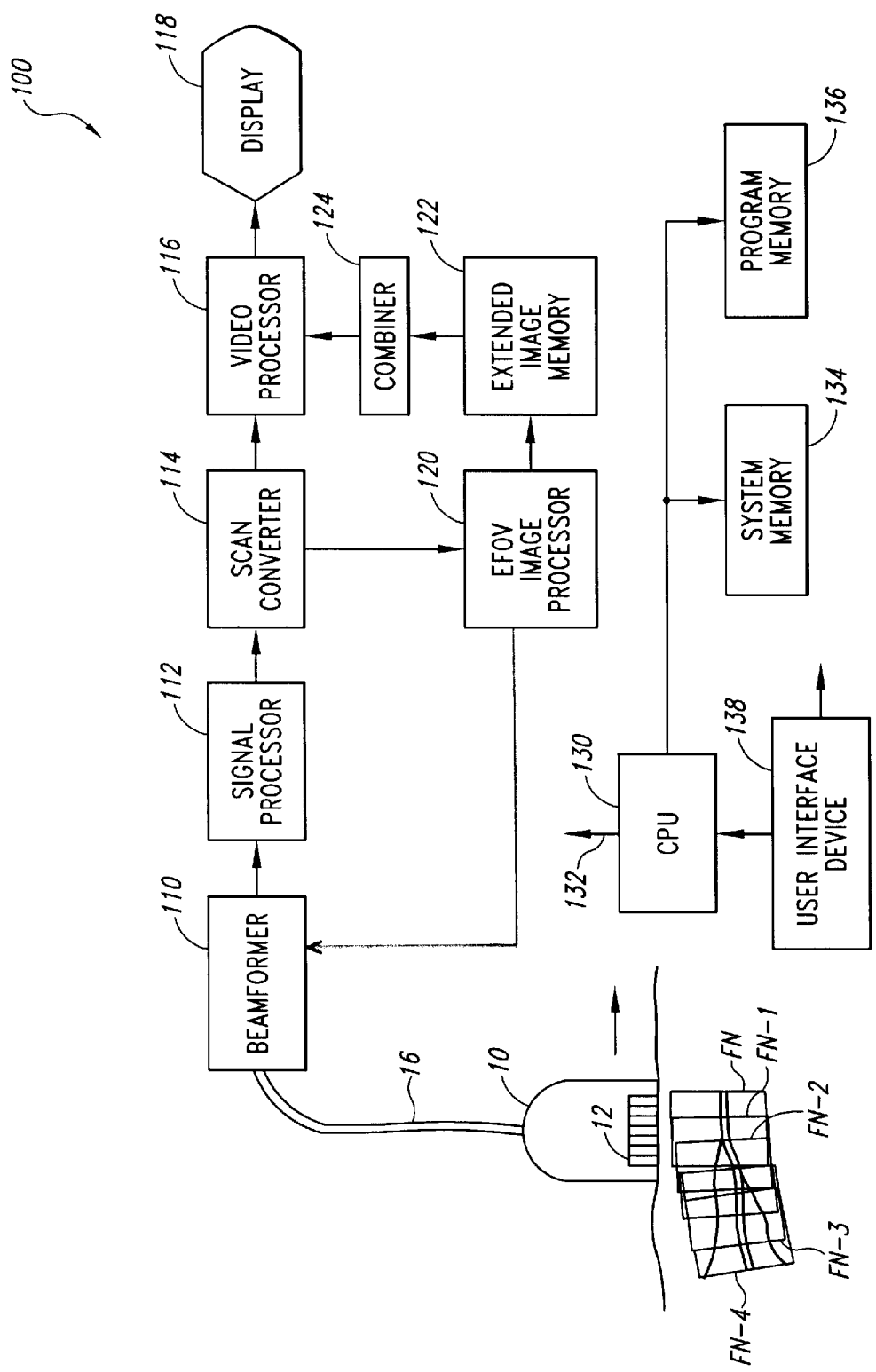
FIG. 7 is a block diagram illustrating an extended field of view ultrasound imaging system in accordance with one embodiment of the invention.

An ultrasound diagnostic imaging system 100 for producing 2-D B-scan EFOV images according to one embodiment of the invention is shown in FIG. 7. Electric signals from the ultrasound scanhead 10 are coupled through the cable 16 and applied to a conventional beamformer 110. The beamformer 110 processes the signals corresponding to ultrasound echoes into a beam that is steered through each 2-D B-scan image frame 50–54 and 60–64. The signals corresponding to the beams are then processed by a signal processor 112 of conventional design and arranged in respective 2-D image frames 50–54 and 60–64 by a scan converter 114. Each image frame 50–54 and 60–64 may be coupled to a video processor 116 and displayed on an image display 118, such as a cathode ray tube or liquid crystal display.

In accordance with one embodiment of the present invention, data corresponding to each 2-D image frame is coupled to an EFOV image processor 120. The EFOV image processor 120 receives and stores data corresponding to each newly acquired 2-D image frame and computes the displacement between one of the partial image frames 60–64 and either another partial image frame 60–64 or one of the full image frames 50–54. The EFOV image processor 120 then stores the aligned image frames in an extended image memory 122. When an EFOV image is to be displayed the aligned images are retrieved from the memory 122, combined by a combiner 124, and coupled to the video processor 116 for viewing on the display 118. Tracking information may also be fed back to the beamformer 110 from the EFOV image processor to enable the beams produced by the scanhead to track features such as speckle.

The operation of the imaging system 100 is preferably controlled by a CPU 130, which is coupled through a bus 132 to various of the components shown in FIG. 7. The CPU 130 is also typically coupled to a system memory 134, such as random access memory ("RAM"), and a program memory 136, such as a read only memory ("ROM"). The program memory 136 stores the program of instructions executed by the CPU 130, and the system memory 134 temporarily stores instructions and data for use by the CPU 130. The system memory 134 may be used to implement the extended image memory 122. A user interface device 138, such as a keyboard, mouse, trackball, or other device, may be manipulated by the clinician to control the operation of the imaging system 100.

Figure 8:
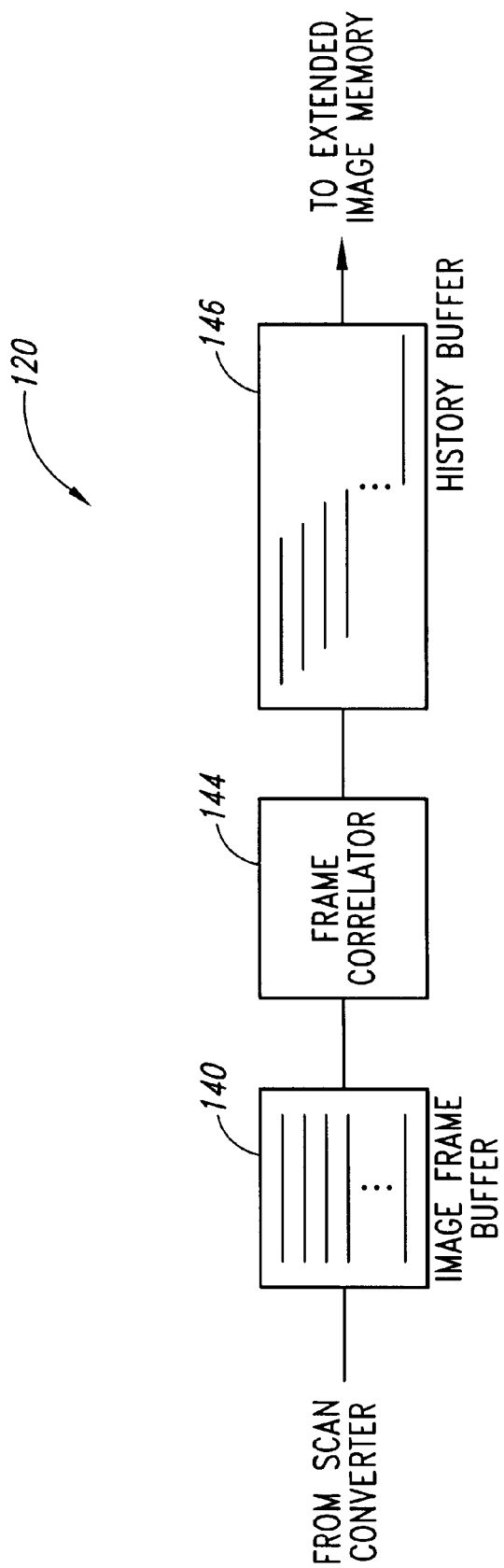
FIG. 8 is a block diagram illustrating one embodiment of an extended field of view image processor used in the extended field of view ultrasound imaging system of FIG. 7.

One embodiment of the EFOV image processor 120 in accordance with the invention is shown in FIG. 8. As mentioned previously, data corresponding to each image frame 50–54 and 60–64 are generated by the scan converter 114 (FIG. 7). This image frame data is applied to and stored in an image frame buffer 140, which may be a dedicated memory, a portion of the system memory 134 used by the CPU 130 or some other memory. The image frame buffer 140 stores all of the data corresponding to each 2-D image frame 50–54 and 60–64 in individually accessed blocks of memory so that data for each image frame may be accessed. The image frame data from the image frame buffer 140 are accessed by a frame correlator 144, which determines the portion of each partial 2-D image frame 60–64 that overlaps portions of either another partial image frame 60–64 or one of the full image frames 50–54. As previously explained, the image frames are correlated with other image frames using the speckle pattern in the image frames through a variety of techniques, including conventional cross-correlation techniques.

After the image frames have been correlated with each other by the frame correlator 144, the data corresponding to each image frame are stored in a history buffer 146 along with data identifying the relative spatial position of each full image frames 50–54. Again, the history buffer 146 may be a dedicated memory, a portion of the system memory 134 used by the CPU 130, the same memory that is used as the image frame buffer 144 or some other memory. The history buffer 146 preferably stores all of the data corresponding to each image frame and its spatial position in individually accessed blocks of memory so that such data for each image frame may be accessed.

The image frame data stored in the history buffer 146 are combined to form data corresponding to a 2-D EFOV B-scan image, and this EFOV image data are stored in the extended image memory 122 (FIG. 7).

Various techniques can be used to improve the quality of the 2-D EFOV B-scan image obtained using the ultrasound imaging system 100. For example, each 2-D image frame 50–56 and 60–64 may be obtained by harmonic ultrasound imaging. It has been known for some time that tissue and fluids have inherent nonlinear properties. Tissue and fluids will, even in the absence of a contrast agent, develop and return their own non-linear echo response signals, including signals at harmonics of the transmitted fundamental. While these non-linear echo components of tissue and fluids are generally not as great in amplitude as the harmonic components returned by harmonic contrast agents, they do exhibit a number of characteristics that have been recognized as being advantageous in conventional ultrasound imaging. In particular, it has been recognized that negligible harmonic signals are generated very close to the transducer, which allows for clutter reduction when imaging through narrow orifices, such as the ribs, since fundamental signal reverberations are not being used for imaging. Additionally, it has been recognized that the levels of a harmonic beam side lobe are lower than the corresponding levels of the side lobes of the fundamental beam, which has implications for off-axis clutter reduction. Finally, it has been recognized that the main lobe of the harmonic is narrower than that of its fundamental, which allows for improved lateral resolution. Examples of harmonic ultrasound imaging are described in U.S. Pat. No. 6,193,662, which is incorporated herein by reference.

In obtaining the 2-D image frames by harmonic imaging, the scanhead 10 (FIG. 1) transmits an ultrasound signal at one frequency and receives and processes echoes from reflectors in each image frame 50–54 and 60–64 at a frequency that is a harmonic of the transmitted ultrasound signal. The resulting 2-D image frames 50–54 obtained by harmonic imaging are then combined as described above to provide a 2-D, EFOV harmonic B-scan ultrasound image.

Still another technique that can be used to obtain each 2-D image frame 50–54 and 60–64 is Doppler imaging. In Doppler imaging, received ultrasound echoes are processed to create an image only if the echoes are produced by reflections from moving reflectors, such as blood. The movement of the reflectors shifts the frequency of the transmitted ultrasound so the signals derived from the received echoes are at the shifted frequency. The received signals are then processed to create the image only if they are at the shifted frequency. The 2-D image frames 50–54 and 60–64 are obtained by Doppler imaging, and are then combined as described above to provide an EFOV Doppler ultrasound image. The Doppler image may be used to display the direction of movement or flow, the Doppler power indicative of flow velocity, combined flow and Doppler power, or some other characteristic.

Figure 9:
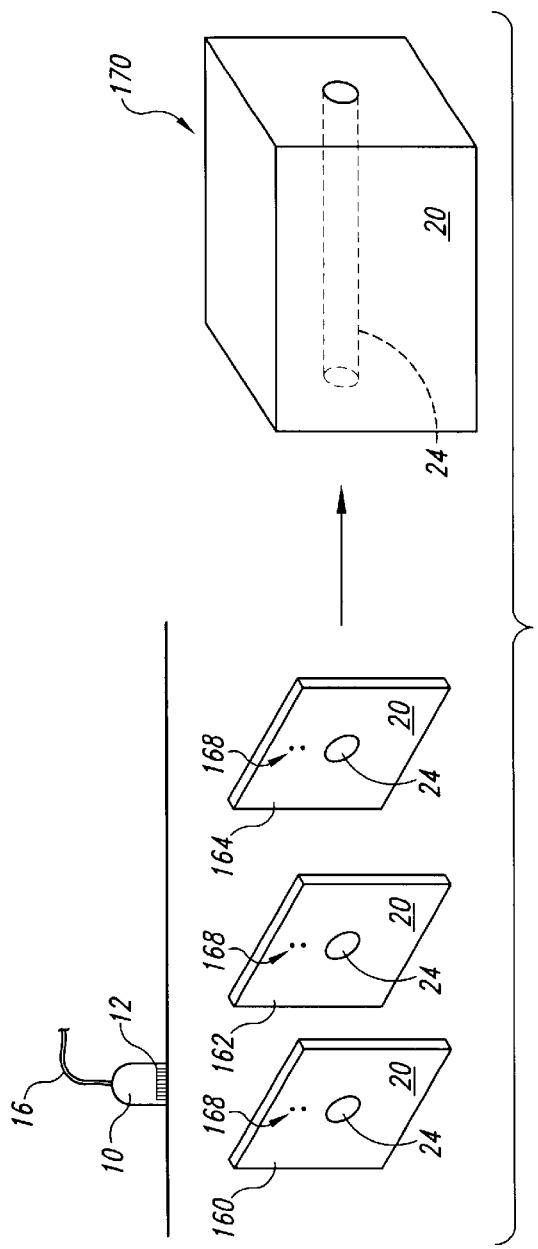
FIG. 9 is an isometric views showing a technique for using the system of FIGS. 7 and 8 to produce a 3-D EFOV image from several 2-D B-scan image frames.

The imaging system of FIGS. 7 and 8 can also be used to create a 3-D EFOV image from 2-D B-scan image frames using a technique shown in FIG. 9. The ultrasound scanhead 10 is moved in a direction that is perpendicular to the linear array 12 (FIG. 1) of the scanhead 10. As a result, successive 2-D B-scan image frames 160, 162, 164 lying in spaced-apart planes that are parallel to each other are acquired. Each image frame 160, 162, 164 is slightly displaced from the previous image frame, but not so much that beam patterns of the image frames 160, 162, 164 do not overlap (although, for purposes of clarity, the overlap is not shown in FIG. 9). As in the other embodiments, the displacement between successive image frames 160, 162, 164 is determined based on speckle 168 in the image frames 160, 162, 164. The image frames 160, 162, 164 are then registered and combined on the basis of the displacements to produce a 3-D EFOV image 170 of the tissues 20 and blood vessel 24.

Figure 10:
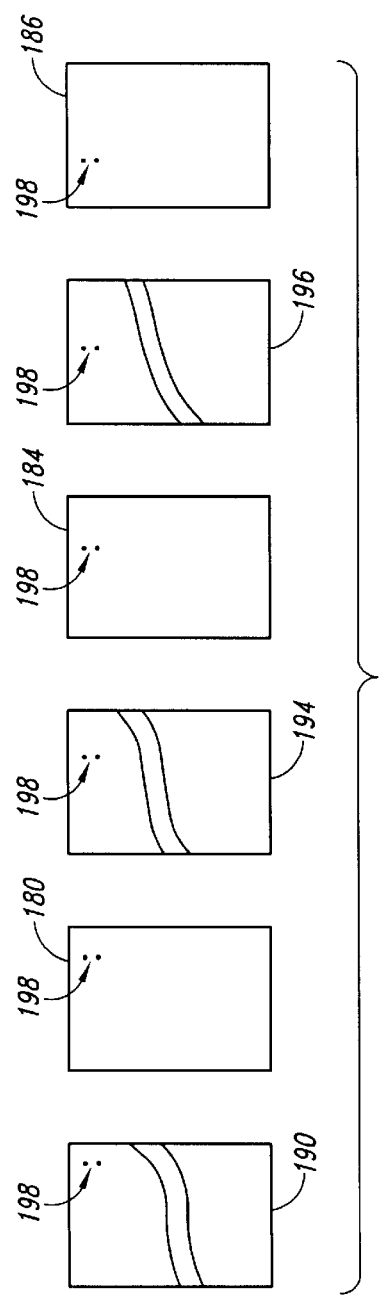
FIG. 10 is a plan view showing a technique for producing a 2-D EFOV Doppler image from several partial 2-D B-scan image frames and several Doppler image frames according to one embodiment of the invention.

Although the embodiments of FIGS. 4–9 have been explained with reference using the same type of image for both the partial image frames 60–64 and the full image frames 50–54, different types of images may be used. For example, as shown in FIG. 10, partial 2-D B-scan image frames 180, 184, 186 are interleaved with full 2-D Doppler image frames 190, 194, 196. Speckle 198 in the B-scan image frames 180, 184, 186, either alone or with the speckle pattern in the Doppler image frames 190, 194, 196, are used to track movement of the scanhead 10, as previously explained.

The advantage of this approach is the partial B-scan image frames 180–186 have substantially less data content than the full Doppler image frames 190–196 for two reasons. First, as with the embodiment of FIGS. 4–8, the data required for a partial image frame may be substantially less than the data required for a full image frame. Second, a B-scan image requires substantially less data than a Doppler image because only intensity, rather than both intensity and color is displayed. As a result, using partial B-scan image frames 180, 184, 186 interleaved with full Doppler image frames 190, 194, 196 greatly increases the frame rate and hence the velocity at which the scanhead 10 can be moved.

The technique of the present invention is particularly useful in 3-D EFOV imaging. Image data for development of a 3-D EFOV image can be acquired by either a ID array transducer or a 2D array transducer. When using a ID array transducer, the transducer probe is moved in the elevation dimension to sweep the scan plane through the volume being imaged. The speckle pattern will generally change rapidly as different tissue is continually entering and leaving the scan plane, but there will generally be sufficient overlap to align the image planes acquired from the volume. In the use of a 2D array, beams can be electronically steered in three dimensions as the probe is moved, enabling volumes of data with overlapping speckle patterns to be acquired in virtually real time.

In the ultrasound system such as that shown in FIG. 7, it may be faster or easier to process the tracking beam data and image data through different signal paths. For instance the tracking beam data may be processed through the color processing channel while the image data is processed through the 2D echo channel, or vice-versa. In a constructed embodiment the imaging beams will generally be adjustable by the user to allow the user to optimize the image quality of the system. The tracking beams will generally be optimized at the factory for tracking and will generally not be user variable. It will be appreciated that image and tracking planes or volumes could be interleaved in time, or that the acquisition of image data can be interrupted on a beam-by-beam basis to enable the time interleaving of tracking and imaging beams.

From the foregoing it will be appreciated that, although specific embodiments of the invention have been described herein for purposes of illustration, various modifications may be made without deviating from the spirit and scope of the invention. For example, although the system 100 stores data corresponding to each image frame in both the image frame buffer 140 and the history buffer 146, it will be understood that it need only be stored in the image frame buffer 140. Accordingly, the invention is not limited except as by the appended claims.

What is claimed is:

1. A method of acquiring an extended field of view ultrasound image, comprising:
   acquiring a first plurality of spatially overlapping ultrasound image data sets by moving an ultrasound scanhead along a target area;
   acquiring a second plurality of spatially overlapping ultrasound image data sets by moving the ultrasound scanhead along the target area, the acquisition of the ultrasound image data sets in the second plurality being interspersed with the acquisition of the ultrasound image data sets in the first plurality, the ultrasound image data sets in the first plurality containing substantially more image data than the ultrasound image data sets in the second plurality;
   using the ultrasound image data sets in the second plurality to track the movement of the ultrasound scanhead based upon the respective locations of corresponding speckle in the ultrasound image data sets in the second plurality; and
   combining at least some of the ultrasound image data sets in the first plurality based on the tracked movement of the ultrasound scanhead to create the extended field of view ultrasound image.

2. The method of claim 1 wherein the act of using the ultrasound image data sets in the second plurality to track the movement of the ultrasound scanhead comprises solely using the ultrasound image data sets in the second plurality to track the movement of the ultrasound scanhead based upon the respective locations of corresponding speckle in the ultrasound image data sets in the second plurality.

3. The method of claim 1 wherein the act of using the ultrasound image data sets in the second plurality to track the movement of the ultrasound scanhead comprises using the ultrasound image data sets in the second plurality in combination with the ultrasound image data sets in the first plurality to track the movement of the ultrasound scanhead based upon the respective locations of corresponding speckle in the ultrasound image data sets in the first and second plurality.

4. The method of claim 1 wherein the ultrasound image data sets in the first and second plurality comprise ultrasound images of the same type.

5. The method of claim 4 wherein the ultrasound images in the first and second plurality comprise B-scan images data sets.

6. The method of claim 1 wherein the ultrasound image data sets in the first plurality are of a different type from the ultrasound image data sets in the second plurality.

7. The method of claim 6 wherein the ultrasound image data sets in the first plurality comprise B-scan image data sets and the ultrasound image data sets in the second plurality comprise Doppler image data sets.

8. The method of claim 1 wherein the act of acquiring a second plurality of spatially overlapping ultrasound image data sets comprises acquiring image frame data from a portion of each image frame in the second plurality based upon the location of speckle in the image frame.

9. The method of claim 1, further comprising displaying the extended field of view ultrasound image.

10. The method of claim 1 wherein the ultrasound image frames in the first plurality are of a different type than the extended filed of view ultrasound image.

11. The method of claim 1 wherein the ultrasound image data sets in the first plurality are 2-D ultrasound image frames, and wherein the extended filed of view ultrasound images are 3-D ultrasound images.

12. The method of claim 1 wherein the ultrasound image data sets in the first plurality are 3-D ultrasound image volumes, and wherein the extended filed of view ultrasound images are 3-D ultrasound images.

13. The method of claim 1 wherein the acts of acquiring the first and second plurality of spatially overlapping ultrasound image data sets comprises acquiring the first and second plurality of spatially overlapping ultrasound image data sets by harmonic imaging.

14. The method of claim 1 wherein the act of acquiring the first plurality of spatially overlapping ultrasound image data sets comprises acquiring the first plurality of spatially overlapping ultrasound image data sets by Doppler imaging.

15. The method of claim 1 wherein the ultrasound scanhead comprises a one-dimensional ultrasound scanhead having a linear array of ultrasound transducer elements.

16. The method of claim 1 wherein the ultrasound image frames in the second plurality are interspersed with the acquisition of the ultrasound image frames in the first plurality on a 1:1 basis.

17. A method of displaying a 3-D extended field of view image, comprising:
    acquiring data corresponding to substantially the entire portion of each image volume in a first set of spatially overlapping ultrasound image volumes;
    acquiring data corresponding to a relatively small part of each image volume in a second set of spatially overlapping ultrasound image volumes, the acquisition of the data corresponding to each image volume in the first set being interspersed with the acquisition of the data corresponding to each image volume in the second set;
    using speckle in each of the image volumes in the second set to determine the displacement of each of the image volumes in the first set;
    registering the image volumes in the first set based upon the determination of the displacement of each of the image volumes in the first set; and
    displaying a plurality of the registered image volumes in the first set, thereby displaying the extended field of view ultrasound image.

18. The method of claim 17 wherein the image volumes in the first set comprise three-dimensional ultrasound image volumes, and wherein the act of registering the image volumes in the first set comprises registering the image volumes to provide a three-dimensional extended field of view image.

19. The method of claim 17 wherein the act of using speckle in each of the image volumes in the second set to determine the displacement of each of the image volumes in the first set comprises processing the speckle using a cross-correlation algorithm.

20. The method of claim 17 wherein the acquisition of the data corresponding to each image volume in the first set is interspersed with the acquisition of the data corresponding to each image volume in the second set on a 1:1 basis.

21. The method of claim 17 wherein the act of acquiring data corresponding to a relatively small part of each image volume in a second set of spatially overlapping ultrasound image volumes comprises acquiring data corresponding to a portion of each image volume based upon the location of speckle in the image volume.

22. A method of registering at least two partially overlapping, substantially complete image frames of ultrasound data, comprising:
    acquiring at least two partially overlapping, partial image frames of ultrasound data obtained at locations intermediate the locations from which the substantially complete image frames of ultrasound data were obtained;
    processing ultrasound data corresponding to speckle in the partial image frames of ultrasound data to determine the displacement between the locations from which the partial image frames of ultrasound data were obtained; and
    based on the determined displacement, combining the ultrasound data from the substantially complete image frames in a manner that causes the combined data to correspond to the substantially complete image frames spatially registered with each other.

23. The method of claim 22 wherein the image frames comprise two-dimensional ultrasound image frames, and wherein the act of combining the ultrasound data from the substantially complete image frames in a manner that causes the combined data to correspond to the substantially complete image frames spatially registered with each other comprises combining the ultrasound data from the substantially complete image frames in a manner that causes the combined data to correspond to a three-dimensional extended field of view image.

24. A method of producing an extended field of view image, comprising:
    acquiring data corresponding to at least two partially overlapping, substantially complete, spatially displaced ultrasound image frames;
    acquiring data corresponding to at least two partially overlapping, partially complete, ultrasound image frames that are spatially displaced and at locations intermediate the locations of the substantially complete ultrasound image frames;
    identifying speckle in the partially complete ultrasound image frames;
    determining the spatial displacement of the partially complete ultrasound image frames based on the location of the identified speckle in each of the partially complete ultrasound image frames;
    determining the spatial displacement of the substantially complete ultrasound image frames based on the determined spatial displacement of the partially complete ultrasound image frames; and
    displaying as the extended field of view image the substantially complete ultrasound image frames registered with each other responsive to the determined spatial displacement of the substantially complete ultrasound image frames.

25. The method of claim 24 wherein the substantially complete, spatially displaced ultrasound image frames and the partially complete, spatially displaced ultrasound image frames comprise two-dimensional ultrasound image frames, and wherein the act of displaying as the extended field of view image the substantially complete ultrasound image frames registered with each other comprises displaying as the extended field of view image the substantially complete ultrasound image frames registered with each other in a manner that causes the substantially complete ultrasound image frames to be displayed as a three-dimensional extended field of view image.

26. An ultrasound imaging system for generating a three-dimensional extended field of view image, the system comprising:
    an ultrasound scanhead structured to generate an electrical signal corresponding to ultrasound echoes;
    a beamformer coupled to the scanhead to generate electrical signals corresponding to ultrasound echoes from beneath the scanhead;
    a scan converter coupled to the beamformer to generate data from the electrical signals corresponding to a plurality of partially overlapping, substantially complete image data sets and a plurality of partially overlapping, partially complete image data sets as the scanhead is scanned across a field of interest, the substantially complete image data sets being interspersed with the partially complete image data sets;
    an image processor coupled to the scan converter, the image processor storing data corresponding to each of the image data sets, the image processor identifying data corresponding to speckle in the partially complete image data sets and using the identified speckle data to track the movement of the ultrasound scanhead, the image processor further processing the data corresponding to the substantially complete image data sets to create image data that corresponds to the substantially complete image data sets registered with each other to form an extended field of view image based upon the tracked movement of the scanhead;

an image memory coupled to the image processor, the image memory storing the image data corresponding to the substantially complete image data sets registered with each other to form an extended field of view image; and a display coupled to the image memory for displaying the extended field of view image.

27. The ultrasound imaging system of claim 26 wherein the image processor comprises:

an image frame buffer coupled to the scan converter, the image frame buffer being structured to store data corresponding to each of the image data sets; and a frame correlator coupled to the image frame buffer, the frame correlator being structured to determine the relative spatial positions of each of the partially complete image data sets based on speckle in the partially complete image data sets and to generate spatial position data corresponding thereto.

28. The ultrasound imaging system of claim 26, wherein the ultrasound scanhead is structured to transmit an ultrasound signal having a fundamental frequency and to receive ultrasound echoes having a frequency that is a harmonic of the fundamental frequency, the beamformer generating the electrical signals from the ultrasound echoes at the harmonic frequency so that the image data sets are produced by harmonic imaging.

29. The ultrasound imaging system of claim 26, wherein the scan converter is structured to generate data from the electrical signals from the beamformer only if the electrical signals have a frequency that is Doppler shifted from the frequency transmitted by the scanhead so that at least the substantially complete image data sets comprise Doppler image data sets.

30. The ultrasound imaging system of claim 26, wherein the image processor is further operable to identify data corresponding to speckle in the substantially complete image data sets and use the identified speckle in both the partially complete image data sets and the substantially complete image data sets to track the movement of the ultrasound scanhead.

31. The ultrasound imaging system of claim 26, wherein the image frames comprise B-scan image frames and the extended field of view images comprise three-dimensional images.

32. The ultrasound imaging system of claim 26, wherein the ultrasound scanhead comprises a one-dimensional ultrasound scanhead having a linear array of ultrasound transducer elements.

33. The ultrasound imaging system of claim 26, wherein beams of the plurality of substantially complete image data sets are interspersed with beams of the plurality of partially complete image data sets.

34. The ultrasound imaging system of claim 26, wherein the ultrasound scanhead comprises a two-dimensional array ultrasound scanhead having a two dimensional array of ultrasound transducer elements.

* * * * *